United States Patent
Holmes et al.

(10) Patent No.: US 11,771,668 B2
(45) Date of Patent: Oct. 3, 2023

(54) NICLOSAMIDE FORMULATIONS AND METHODS OF USE

(71) Applicant: FLORIDA STATE UNIVERSITY RESEARCH FOUNDATION, INC., Tallahassee, FL (US)

(72) Inventors: Eric Holmes, Tallahassee, FL (US); Gary Ostrander, Tallahassee, FL (US)

(73) Assignee: FLORIDA STATE UNIVERSITY RESEARCH FOUNDATION, INC., Tallahassee, FL (US)

(*) Notice: Subject to any disclaimer, the term of this patent is extended or adjusted under 35 U.S.C. 154(b) by 12 days.

(21) Appl. No.: 17/301,444

(22) Filed: Apr. 2, 2021

(65) Prior Publication Data

US 2021/0308079 A1    Oct. 7, 2021

Related U.S. Application Data

(60) Provisional application No. 63/004,353, filed on Apr. 2, 2020.

(51) Int. Cl.

| | |
|---|---|
| *A61K 31/167* | (2006.01) |
| *A61K 47/10* | (2017.01) |
| *A61K 47/20* | (2006.01) |
| *A61K 47/40* | (2006.01) |
| *A61K 9/48* | (2006.01) |
| *A61K 9/28* | (2006.01) |
| *A61K 9/00* | (2006.01) |
| *A61K 47/38* | (2006.01) |
| *A61K 47/32* | (2006.01) |

(52) U.S. Cl.
CPC ............ *A61K 31/167* (2013.01); *A61K 9/006* (2013.01); *A61K 9/009* (2013.01); *A61K 9/0095* (2013.01); *A61K 9/284* (2013.01); *A61K 9/2866* (2013.01); *A61K 9/4816* (2013.01); *A61K 9/4891* (2013.01); *A61K 47/10* (2013.01); *A61K 47/20* (2013.01); *A61K 47/32* (2013.01); *A61K 47/38* (2013.01); *A61K 47/40* (2013.01)

(58) Field of Classification Search
CPC ...... A61K 31/167; A61K 9/006; A61K 9/009; A61K 9/0095; A61K 9/284; A61K 9/2866; A61K 9/4816; A61K 9/4891; A61K 47/10; A61K 47/20; A61K 47/32; A61K 47/38; A61K 47/40
See application file for complete search history.

(56) References Cited

U.S. PATENT DOCUMENTS

| | | | |
|---|---|---|---|
| 2011/0206764 A1* | 8/2011 | Holmes | A61K 9/0053 424/463 |
| 2018/0133208 A1* | 5/2018 | Cardelli | A61K 31/46 |
| 2018/0289805 A1* | 10/2018 | Peyman | A61K 45/06 |
| 2020/0276214 A1* | 9/2020 | Waters | A61K 31/609 |

* cited by examiner

*Primary Examiner* — Robert A Wax
*Assistant Examiner* — Olga V. Tcherkasskaya
(74) *Attorney, Agent, or Firm* — THOMAS | HORSTEMEYER, L.L.P.

(57) ABSTRACT

The present invention concerns compositions comprising at least one niclosamide compound, such as niclosamide or a pharmaceutically acceptable salt thereof, and at least one permeability enhancer, such as glycerol or dimethylpalmityl-ammonio propanesulfonate (PPS), and their use of such compositions as niclosamide agents. Advantageously, the niclosamide compound is capable of being transported across a Caco-2 cell membrane by at least 150% relative to the amount capable of being transported across the Caco-2 cell membrane in the absence of the permeability enhancer. Compositions, including oral dosage forms, and methods for delivering niclosamide compounds, such as for treatment or prevention of human coronavirus infections, are also provided.

4 Claims, 1 Drawing Sheet

NICLOSAMIDE FORMULATIONS AND METHODS OF USE

CROSS-REFERENCE TO RELATED APPLICATION

The present application claims the benefit of U.S. Provisional Application Ser. No. 63/004,353, filed Apr. 2, 2020, which is hereby incorporated by reference herein in its entirety, including any figures, tables, nucleic acid sequences, amino acid sequences, or drawings.

BACKGROUND OF THE INVENTION

Coronaviruses are enveloped viruses of the family Coronaviridae, which are transmitted through the air and primarily infect the cells of the upper respiratory and gastrointestinal tract of mammals and birds. The name coronavirus is derived from the Latin "crown" or "halo", which refers to its characteristic morphology, which resembles a crown or solar corona when imaged using an electron microscope.

Coronaviruses cause illness in adults and children ranging from the common cold to more severe diseases. Common signs of infection include respiratory symptoms, fever, cough, shortness of breath, and breathing difficulties. In more severe cases, coronavirus infection can cause pneumonia, severe acute respiratory syndrome (SARS), kidney failure, and even death. The widely publicized human coronavirus discovered in 2003, SARS-CoV, causes both upper and lower respiratory tract infections.

Coronaviruses are zoonotic, meaning they are transmitted between animals and humans. Several known coronaviruses are circulating in animals that have not yet infected humans. A novel coronavirus (nCoV) is a new strain that has not been previously identified in humans. There are currently no vaccines or antiviral drugs to prevent or treat human coronavirus infections.

Following the outbreak of SARS in 2003, which had begun the prior year in Asia, and secondary cases elsewhere in the world, the World Health Organization (WHO) issued a press release stating that a novel coronavirus identified by a number of laboratories was the causative agent for SARS. The virus was officially named the SARS coronavirus (SARS-CoV).

In September 2012, a new type of coronavirus was identified, initially called Novel Coronavirus 2012, and now officially named Middle East respiratory syndrome coronavirus (MERS-CoV). After the Dutch Erasmus Medical Centre sequenced the virus, the virus was given the name Human Coronavirus-Erasmus Medical Centre (HCoV-EMC). The final name for the virus is Middle East respiratory syndrome coronavirus (MERS-CoV).

In May 2014, two United States cases of MERS-CoV infection were recorded, both occurring in healthcare workers who worked in Saudi Arabia and then traveled to the U.S. In May 2015, an outbreak of MERS-CoV occurred in the Republic of Korea, when a man who had traveled to the Middle East, visited hospitals in the Seoul area to treat his illness, causing one of the largest outbreaks of MERS-CoV outside the Middle East.

In December 2019, a pneumonia outbreak was reported in Wuhan, China, and was traced to a novel strain of coronavirus, which was given the interim name 2019-nCoV by the World Health Organization (WHO), later renamed SARS-CoV-2 by the International Committee on Taxonomy of Viruses (Zhu N. et al, "A Novel Coronavirus from Patients with Pneumonia in China, 2019", *N Engl J Med*, February 2020, 382(8):727-733, Epub 24 Jan. 2020). Coronavirus disease 2019 (COVID-19), formerly known as 2019-nCoV acute respiratory disease, is the infectious disease caused by SARS-CoV-2. SARS-CoV-2 has killed more people than 2003 SARS outbreak. Some researchers have suggested that the Huanan Seafood Market may not be the original source of viral transmission to humans.

A new virus variant has one or more genetic distinctions (e.g., mutations) that differentiate it from the wild-type or predominant virus variants already circulating among the general population, and several variants of SARS-CoV-2 have been reported in the United States and globally in 2020. Some of the SARS-CoV-2 variants that have emerged are particularly concerning, including at least B.1.1.7 identified in the United Kingdom, B.1.351 identified in South Africa, and P.1 identified in travelers from Brazil.

There remains a need for a safe and effective method of treating or preventing infections of coronavirus and associated symptoms, in particular those related to COVID-19, and its causative agent, SARS-CoV-2, and its variants.

Niclosamide (5-chloro-N-2-chloro-4-nitrophenyl)-2-hydroxybenzamide) is an oral anti-helminthic drug used to treat tapeworm infections since the 1960s. More recently, niclosamide has been observed to have anti-cancer activity, as well as the ability to inhibit some viral infections. Niclosamide is a Class IV drug under the biopharmaceutical classification system (BCS), having low permeability and low solubility (Saffoon N. et al., *Journal of Applied Pharmaceutical Science*, 2011, 01(07):13-20); consequently, the compound has low systemic bioavailability when administered orally. This can be beneficial for treating local parasitic infections of the intestines while minimizing system exposure; however, poor bioavailability is an obstacle to further clinical development of niclosamide for other indications.

BRIEF SUMMARY OF THE INVENTION

The invention concerns compositions comprising at least one niclosamide compound (niclosamide or a derivative thereof) and at least one permeability enhancer. The compositions can increase the amount of a niclosamide compound capable of being transported across a cell membrane such as a Caco-2 cell membrane. In some embodiments, the compositions can increase this amount by at least 150% relative to the amount capable of being transported across the cell membrane in the absence of the permeability enhancer.

Suitable permeability enhancers for use in the compositions include, but are not limited to, fatty acids, fatty acid esters, fatty acid salts, glycerol, glycerol monocaprylate, surfactants, cyclodextrins, sodium salicylate, ethylenediamine tetraacetic acid, citric acid, chitosan, chitosan derivatives, N-trimethyl chitosan chloride, monocarboxymethylchitosan, palmitoyl carnitine chloride, acyl carnitines, ethylene glycol tetraacetic acid, 3-alkylamido-2-alkoxypropyl-phosphocholine derivatives, dimethylpalmityl-ammonio propanesulfonate, alkanoylcholines, N-acetylated amino acids, mucoadhesive polymers, phospholipids, piperine, 1-methylpiperazine, alpha.-amino acids, or mineral oil.

The invention also provides oral dosage forms of the compositions, which comprise a therapeutically effective amount of at least one niclosamide compound and a permeability-enhancing amount of at least one permeability enhancer. The oral dosage forms can further comprise an enteric, or pH-sensitive, coating or layer surrounding the composition. In the oral dosage forms, the permeability enhancer can be, for example, glycerol, glycerol monocaprylate, or dimethylpalmityl-ammonio propanesulfonate. The permeability enhancer can be present in the composition at a concentration from about 5% to about 95% of the combined weight of the niclosamide compound and the permeability enhancer.

In some embodiments of the composition, the composition comprises a packaged dosage formulation or a kit for treatment or prevention of a human coronavirus infection.

Another aspect of the invention concerns kits comprising, in one or more containers, at least one niclosamide compound and at least one permeability enhancer, together in the same container or in separate containers. A kit of the invention can also comprise one or more other compounds, biological molecules, or drugs. In one embodiment, the kit of the invention further comprises one or more of a drug or composition used in treating a viral infection (e.g., a human coronavirus infection, such as SARS-CoV-2 or a variant thereof).

The compositions of the invention exhibit increased bioavailability relative to niclosamide compositions that do not include a permeability enhancer, and may be contacted with human or non-human animal cells in vitro or in vivo, or administered to human or non-human animal subjects in any situation in which delivery of a niclosamide compound may be desired, such as for the treatment of conditions for which niclosamide may be used, such as treatment of parasitic infections, bacterial infections, viral infections, and cancer. The compositions and methods of the invention are particularly useful in situations or settings in which delivery of a niclosamide compound with enhanced bioavailability is desired.

One aspect of the invention concerns a method for delivering a niclosamide compound to a human or non-human animal subject. In some embodiments, the delivery method provides a method for treating or preventing human coronavirus infections, such as SARS-CoV-2 or a variant thereof. Generally, the methods comprise administering to a human or non-human animal subject in need thereof a composition comprising at least one niclosamide compound and at least one permeability enhancer, including oral dosage forms of such compositions. In the compositions used in the methods, the permeability enhancer can be glycerol, glycerol monocaprylate or dimethylpalmityl-ammonio propanesulfonate (PPS), among others, and the niclosamide compound can be one encompassed by a formula in FIGS. 1A-1D. In some embodiments, the at least one niclosamide compound of the composition comprises or consists of niclosamide or a pharmaceutically acceptable salt thereof. In some embodiments, the at least one niclosamide compound of the composition comprises or consists of a niclosamide derivative. In some embodiments, the derivative is a pro-drug, such as p-niclosamide.

In some embodiments, the composition comprising at least one niclosamide compound and at least one permeability enhancer is administered to a human subject infected by a human coronavirus, such as SARS-CoV-2 or a variant thereof, as therapy. In some embodiments, the subject has the disease COVID-19. In other embodiments, the composition comprising at least one niclosamide compound and at least one permeability enhancer is administered to a human subject not infected by human coronavirus, such as SARS-CoV-2 or a variant thereof, as prophylaxis (to prevent or delay the onset of human coronavirus infection).

Another aspect of the invention concerns a method for delivering a niclosamide compound to a human or non-human animal cell, comprising contacting the cell in vitro or in vivo with a composition comprising at least one niclosamide compound and at least one permeability enhancer. In some embodiments, the delivery method provides a method for inhibiting a human coronavirus infection, such as SARS-CoV-2 or a variant thereof, in a human cell, comprising contacting the cell in vitro or in vivo with the composition comprising at least one niclosamide compound and at least one permeability enhancer, before or after the cell is infected with the coronavirus.

In some embodiments of the methods of the invention, the human coronavirus is selected from among SARS-CoV-2, SARS-CoV, and MERS-CoV.

In some embodiments of the methods of the invention, the human coronavirus is a variant of SARS-CoV-2, such as the B.1.1.7 variant, B.1.351 variant, P.1 variant, B.1.427 variant, and B.1.429 variant.

In some embodiments of the methods of the invention, the human coronavirus is a common human coronavirus, such as type 229E, NL63, OC43, and HKU1.

In some embodiments of the methods of the invention, the at least one niclosamide compound of the composition comprises or consists of niclosamide or a pharmaceutically acceptable salt thereof. In some embodiments of the methods of the invention, the at least one niclosamide compound of the composition comprises or consists of a niclosamide derivative. In some embodiments, the derivative is a pro-drug, such as p-niclosamide.

DETAILED DESCRIPTION OF THE INVENTION

Figure 1A:
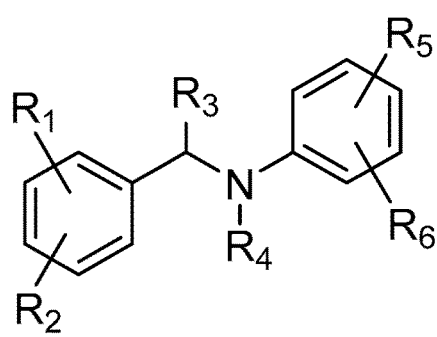
FIGS. 1A-1D. Formulas encompassing niclosamide and derivatives of niclosamide (Formulas 1-4, respectively).

An aspect of the invention concerns a composition comprising at least one niclosamide compound, such as niclosamide or a pharmaceutically acceptable salt thereof, and at least one permeability enhancer, such as glycerol or dimethylpalmityl-ammonio propanesulfonate (PPS).

Another aspect of the invention concerns a method for delivering a niclosamide compound to a human or non-human animal subject, comprising administering to the human or non-human animal subject an effective amount of a composition comprising at least one niclosamide compound, such as niclosamide or a pharmaceutically acceptable salt thereof, and at least one permeability enhancer, such as glycerol or dimethylpalmityl-ammonio propanesulfonate (PPS). In some embodiments, the delivery method is a method for treatment or prevention of a human coronavirus infection, such as SARS-CoV-2, in a human subject, comprising administering to the human subject an effective amount of a composition comprising at least one niclosamide compound, such as niclosamide or a pharmaceutically acceptable salt thereof, and at least one permeability enhancer, such as glycerol or PPS. The composition may be administered to the human subject before or after initiation of the coronavirus infection, thereby treating the coronavirus infection. In some embodiments, the subject has the disease COVID-19 at the time composition is administered. The subject may be symptomatic or non-symptomatic.

Another aspect of the invention concerns a method for delivering a niclosamide compound to a human or non-human animal cell. In some embodiments, the method is a method for inhibiting a human coronavirus infection in a human cell, comprising contacting the cell in vitro or in vivo with a composition comprising at least one niclosamide compound, such as niclosamide or a pharmaceutically acceptable salt thereof, and at least one permeability enhancer, such as glycerol or dimethylpalmityl-ammonio propanesulfonate (PPS), before or after the cell is infected with the coronavirus. When carried out in vivo, the composition is administered to a human or non-human animal subject. Optionally, when carried out in vivo, the method for inhibiting a human coronavirus infection in human cells may be used to treat or prevent the human coronavirus in accordance with the method of treatment herein.

The human coronavirus may be any type or subgroup, including alpha, beta, gamma, and delta. In some embodiments of the aforementioned methods of the invention, the human coronavirus is selected from among SARS-CoV-2, SARS-CoV, and MERS-CoV. In some embodiments of the aforementioned methods of the invention, the human coronavirus is a common human coronavirus, such as type 229E, NL63, OC43, and HKU1.

Without intending to be limited to any particular theory or mechanism of action, it is believed that one or more polar groups on niclosamide limit permeability of the compound, and this is particularly problematic where the niclosamide compound is not or is only weakly transported across the cell membrane by a transport protein. The inventors propose that inclusion of one or more permeability enhancer compounds in formulations with niclosamide compounds that are poorly absorbed, can increase the amount of niclosamide compound that is absorbed by cells, and ultimately increase the bioavailability to the organism. In particular, permeability enhancer compound(s) are believed to provide niclosamide compounds with improved oral efficacy with respect to absorption across cellular membranes. Without wishing to be bound by any particular theory or mechanism of action, it is believed that a permeability enhancer compound may facilitate increased absorption of polar niclosamide compounds through cellular tight junctions, may act to promote absorption through a transcellular pathway, or may act to increase permeability through other mechanisms. Accordingly, the invention provides a composition and method for improving oral bioavailability and activity of niclosamide compounds.

"Polar" compounds/agents, such as a niclosamide compound, are those that have at least one group that confers a degree of partial or permanent charge on the compound that is greater than or equal to the charge of a hydroxyl group, more preferably greater than or equal to the charge of a carboxyl group, more preferably greater than or equal to the charge of an imidazole group, more preferably greater than or equal to the charge of an amino group, and more preferably greater than or equal to the charge of a guanidino group, phosphate, or sulfate group.

With respect to a composition aspect of this invention, there is provided a composition comprising at least one niclosamide compound and at least one permeability enhancer, wherein the composition provides a Caco-2 niclosamide compound permeability at least 150% of the permeability observed in compositions that do not have a permeability enhancer. An enhancement in permeability of 150% is also the equivalent of a 1.5-fold improvement in niclosamide compound permeability. In some embodiments, the niclosamide compound is niclosamide or a pharmaceutically acceptable salt of niclosamide.

The composition of this invention also contemplates an oral composition comprising a therapeutically effective amount of at least niclosamide compound and a permeability-enhancing amount of a permeability enhancer. In this aspect, the enhancing amount of permeability enhancer compound(s) is an amount or concentration which produces a Caco-2 niclosamide compound permeability at least 150% of (i.e., 1.5-fold over) that provided by the niclosamide compound in the absence of a permeability enhancer(s).

The invention also provides a method for improving the oral bioavailability of niclosamide compounds that are not absorbed or only weakly absorbed through a cell membrane. Generally, such methods comprise providing a pharmaceutical formulation comprising a therapeutically effective amount of at least one niclosamide compound and a permeability-enhancing amount of one or more suitable permeability enhancer compounds in a pharmaceutical formulation or dosage form thereof which is suitable for oral administration. Examples of suitable forms include, for example, capsules, tablets, caplets, softgels, various sustained or controlled release dosage forms, solutions, suspensions, and the like, each of which may include acceptable pharmaceutical excipients which are well known to those skilled in the art and suitable for formulation of the dosage form in question.

As used herein, the term "permeability enhancer," "enhancer" and variations thereof refer to compounds which improve the bioavailability of niclosamide when incorporated into oral formulations. In some embodiments, a niclosamide permeability enhancer may be defined as a compound capable of increasing the rate of niclosamide compound transport across a Caco-2 cell membrane by 1.5-fold (150%) or more compared to the same niclosamide compound transport rate in the absence of the enhancer compound. Any means known or otherwise available to those of skill in the art can be used to determine the transport rate, including those Caco-2 cell permeability assays described and exemplified herein.

With respect to the bioavailability of the niclosamide compounds, the presence of a permeability enhancer increases the bioavailability of the niclosamide compound to the subject relative to the bioavailability of the niclosamide compound in the absence of the permeability enhancer. Thus, in some aspects, the presence of the permeability enhancer increases bioavailability of the niclosamide compound about 1.5 times the amount of bioavailability of the niclosamide compound in the absence of the permeability enhancer, more preferably, the presence of the permeability enhancer increases bioavailability of the niclosamide compound by about 2 times, more preferably about 2.5 times, more preferably about 3 times, more preferably about 3.5 times, more preferably about 4 times, more preferably about 4.5 times, more preferably about 5 times, more preferably about 6 times, more preferably about 7 times, more preferably about 8 times, more preferably about 9 times, more preferably about 10 times, more preferably about 12 times, more preferably about 15 times, more preferably about 17 times, more preferably about 20 times, more preferably about 22 times, more preferably about 25 times, more preferably about 27 times, more preferably about 30 times or even greater times the amount of bioavailability of the niclosamide compound in the absence of the permeability enhancer.

The invention contemplates that niclosamide compounds having low bioavailability in the absence of a permeability enhancer will have enhanced bioavailability when combined with a permeability enhancer in a formulation. It is desirable that the bioavailability of the one or more niclosamide compound be enhanced to at least about 10% in the subject to which the niclosamide compound is administered, more preferably at least about 15%, more preferably at least about 20%, more preferably at least about 25%, more preferably at least about 30%, more preferably at least about 35%, more preferably at least about 40%, more preferably at least about 45%, more preferably at least about 50%, more preferably at least about 55%, more preferably at least about 60%, more preferably at least about 65%, more preferably at least about 70%, and more preferably at least about 75% or more in the subject to which the niclosamide compound is administered, when formulated with a permeability enhancer.

A variety of classes of compounds may serve as suitable permeability enhancers according to the invention. A first category includes fatty acids and salts and esters thereof, including mono-, di-, and triglycerides. Medium chain length fatty acids, especially C8 and C10 acids, and their salts and esters are particularly useful. Suitable specific examples include sodium caprylate, sodium caprate, medium chain length fatty acids and their salts and esters sold under the trademark CAPMUL™ glycerides (available from Abitec of Columbus, Ohio), medium chain length fatty acids and their salts and esters sold under the trademark LABRASOL™ glycerides (PEG-8 caprylic/capric glycerides, available from Gattefosse SAS of Saint Priest, Cedex, France), medium chain length fatty acids and their salts and esters sold under the trademark GELUCIRE™ 44/14 (PEG-32 glyceryl laurate EP, available from Gattefosse), other glycerides & fatty acid esters, medium chain length fatty acids and their salts and esters sold under the trademark CREMOPHOR™ (BASF, Ludwigshafen, Germany), D-.alpha.-tocopheryl polyethylene glycol 1000 succinate, vegetable oils, polyoxylglycerides, and medium chain mono- and diacylglycerides.

One example of this class, a medium chain length fatty acid or its salt or ester sold under the trademark CAPMUL™ MCM L8 (glycerol monocaprylate) (available from Abitec of Columbus, Ohio), is composed of mono- and diglycerides of medium chain fatty acids (mainly caprylic, with some capric) and 7% maximum free glycerol. It contains at least 44% alpha monoglycerides (as caprylate).

Other examples of this class of medium chain length fatty acids and their salts or esters enhancers include those compositions sold under the trademark GATTEFOSSE® 61A through 61H which are proprietary to Gattefosse SAS, but generally are composed of mixtures containing one or more of medium chain mono-, di-, or triglycerides, polysorbate derivatives, polyoxyl castor oil derivatives, polyethylene glycol derivatives including polyethylene glycol glycerides, polyoxyl ethers, vegetable oils, and similar GRAS (generally regarded as safe) lipidic components in varying amounts.

While not falling directly within this class, glycerol itself may be used for permeability enhancement.

A second category of enhancers includes surfactants having a steroidal structure, such as bile acid salts. Examples of suitable compounds include sodium cholate, sodium deoxycholate, glycocholate, glycoursodeoxycholate, taurocholate, taurodeoxycholate, and steroid detergents/bile salts. Other surfactants may also be suitable permeability enhancers, including cationic, anionic, and nonionic surfactants. Examples include polysorbate 80, hexadecyldimethylbenzylammonium chloride, N-hexadecylpyridinium bromide, dodecyltrimethylammonium bromide, hexadecyltrimethylammonium bromide, tetradecyl-.beta.-D-maltoside, octylglucoside, glycyrrhetinic acid, 3-(N,N-dimethylpalmitylammonio)propanesulfonate, and sodium lauryl sulfate.

Cyclodextrins may also be used as suitable enhancers. Examples include beta-cyclodextrin, hydroxypropyl-beta-cyclodextrin, gamma-cyclodextrin, and hydroxypropyl-gamma-cyclodextrin.

A variety of other compounds may also be used as enhancers. Examples include sodium salicylate, ethylenediamine tetraacetic acid (EDTA), citric acid, chitosan & chitosan derivatives, N-trimethyl chitosan chloride, monocarboxymethyl-chitosan, palmitoyl carnitine chloride, acyl carnitines, ethylene glycol tetraacetic acid (EGTA), 3-alkylamido-2-alkoxypropyl-phosphocholine derivatives, alkanoylcholines, N-acetylated amino acids (based on .alpha.- and non-.alpha.-amino acids), mucoadhesive polymers, phospholipids, piperine, 1-methylpiperazine, .alpha.-amino acids, and mineral oil.

Thus a wide variety of enhancer compounds may be selected from the group consisting of fatty acids, fatty acid esters, fatty acid salts, glycerol, surfactants, cyclodextrins, sodium salicylate, ethylenediamine tetraacetic acid, citric acid, chitosan, chitosan derivatives, N-trimethyl chitosan chloride, monocarboxymethyl-chitosan, palmitoyl carnitine chloride, acyl carnitines, ethylene glycol tetraacetic acid, 3-alkylamido-2-alkoxypropyl-phosphocholine derivatives, alkanoylcholines, N-acetylated amino acids, mucoadhesive polymers, phospholipids, piperine, 1-methylpiperazine, .alpha.-amino acids, and mineral oil.

The above examples of permeability enhancers are exemplary only and do not constitute a complete list of potential permeability enhancers. Any compound capable of increasing the oral absorption of a niclosamide compound by at least 50% is considered to be within the scope of this invention.

The one or more permeability enhancers and one or more niclosamide compounds may be mixed in any proportion so long as there is provided a therapeutically effective amount of the niclosamide compound(s) and a permeability-enhancing amount of the enhancer compound. Enhancement in bioavailability of orally administered niclosamide compounds can depend on the nature and concentration of the enhancer compound with which the niclosamide compound is formulated. It is thus contemplated that the required therapeutic amount may be contained in a single dosage form or divided between one or more dosages intended for ingestion at the same time or in sequence.

The permeability enhancers act relatively independently of the concentration of niclosamide compound(s). Differing permeability enhancers can reach either optimal or maximum enhancement over a wide concentration range depending on their particular inherent enhancement potential. Often, enhancers have a non-linear dose response relationship between concentration of enhancer present and amount of increased niclosamide compound absorption. The amount of enhancer to be utilized in an oral dosage form with a niclosamide compound is initially based upon the enhancement properties observed in Caco-2 cell assays at varying fixed enhancer concentrations. Based upon those results, an effective in vivo amount of enhancer compound for a human formulation can be estimated, demonstrated and optimized without undue experimentation using methods well known to those skilled in the formulation art, to achieve a desired pharmacokinetic in vivo profile.

In formulating the composition of this invention, it will be apparent to those skilled in the formulation art that more effective enhancer compounds would require less niclosamide compound than less effective permeability enhancers to achieve a target pharmacokinetic profile. Given those considerations and variations, the amount of enhancer may be at least about 0.1 wt % of the combined weight of enhancer and niclosamide compound, more preferably at least about 50 wt %, and more preferably at least 70 wt % of the combined weight of enhancer and niclosamide compound. The amount is preferably at most 95 wt %, more preferably at most 80 wt %, and more preferably at most 75 wt % of the combined weight of the enhancer and niclosamide compound. Thus, as shown in the examples, a typical dosage form may contain a wide range of concentrations of enhancer compounds depending on the compound itself and its efficacy in enhancing the permeability of niclosamide compounds following oral administration. Concentrations as low as 0.001% by weight up to 20% may be effective in enhancement of the permeability of niclosamide compounds.

Suitable excipients are well known to those skilled in the formulation art, and any excipient or combination of excipients known in the pharmaceutical art may be used. Examples may include flow aids, stabilizers, surface active agents, binders, dispersing agents, flavorings, taste masking agents, coatings, release control agents, water, and/or other excipients typically employed for formulation of oral dosage forms. In some embodiments, the excipient may comprise one or more materials selected from the group consisting of microcrystalline cellulose, dicalcium phosphate, lactose, pre-gelatinized starch, carnauba wax, candelilla wax, silica, and magnesium stearate.

The compositions of this invention may in some aspects be prepared by combining one or more niclosamide compounds with suitable amounts of either a single permeability enhancer compound or combinations thereof and optionally with other formulation additives/excipients, mixing thoroughly, and either tableting or filling a suitable hard shell capsule or softgel capsule with the resulting composition. In some cases, sonicating the mixture (i.e., exposure of the niclosamide compound/enhancer mixture to ultrasonic radiation) may increase the efficacy of the enhancer. Common methods for sonication are known in the art, such as use of a probe or bath sonicator.

In some cases, high-energy blending of the mixture (e.g., exposing the mixture to significant sheer forces) may increase the efficacy of the enhancer. Common methods for high-energy blending include any known in the art, such as stirrers, rotor-stator devices or colloid mills.

In some cases, homogenization or micronization of the mixture (e.g., exposing the mixture to extreme pressure and stress forces, including but not limited to sheer, turbulence, acceleration and impact forces) may increase the efficacy of the enhancer by forming an emulsion of the niclosamide compound/enhancer mixture in water. Common methods for micronization include any known in the art, such as use of a high pressure homogenizer. Such micronization techniques may significantly reduce the particle size of the mixture in the formulation, providing particle sizes typically <10 μm in size. For example, a glycerol monocaprylate sold under the trademark CAPMUL™ MCM L8 and niclosamide compound mixture may be emulsified in about an equal weight of water. This may be done by repeatedly squirting the mixture through a narrow orifice until an emulsion is formed, or by other emulsion-forming techniques known to those of skill in the art. Although a roughly equal weight of water typically works well, other proportions may also be used according to the invention.

All such methods of sonication, high-energy blending, homogenization and micronization may alter the viscosity of the mixture. In some cases, the viscosity of the mixture may be significantly increased, sometimes by as much as 50% or more. In some cases, an increase in viscosity may be desirable for improved manufacturability (i.e., improved efficiency of filling solid dosage form vessels such as capsules or softgels) or improved content uniformity and decreased variability of the mixture. In some aspects, a significant increase in viscosity may increase the efficacy of the enhancer.

In some aspects, a significant increase in viscosity may indicate a successful endpoint of high-energy mixing, sonication or homogenization. In some cases of homogenization, micronization, sonication or high-energy blending of the mixture, an endothermic reaction may accompany the increase in viscosity. In some embodiments, an endothermic reaction may indicate a successful endpoint of high-energy mixing, sonication or homogenization.

The resulting compositions are typically viscous liquids or paste-like solids. Additional permeability enhancers or formulation additives can either be added prior to sonication or after sonication of the initial lipid/niclosamide compound composition.

In some embodiments, a tablet, multiparticulate dosage form, capsule, softgel, or granule containing the composition may be coated with an enteric or pH-sensitive layer to facilitate niclosamide compound release in the gastro-intestinal tract distal to the stomach. In some embodiments, the enteric coating or pH-sensitive layer may comprise, but is not limited to, one or more materials selected from among the group of enteric polymers including cellulose acetate phthalate, cellulose acetate trimellitate, hydroxypropyl methylcellulose acetate succinate, hydroxypropyl methylcellulose phthalate, and polyvinyl acetate phthalate; and anionic polymers based on methacrylic acid and methacrylic acid esters.

This disclosure contemplates a formulation composition comprising at least one niclosamide compound, a permeability enhancer, and optionally other excipients in a tablet, capsule, softgel, or other solid, liquid, or semi-solid configuration with optional enteric coating. In some embodiments, such compositions are non-aqueous in that water is excluded as a potential excipient and the only water that is present is that which may be present natively or naturally in the individual formulation components. It is also contemplated that the viscosity of liquid formulations for capsule delivery applications according to the invention will be higher than the viscosity of a 5% aqueous solution of that formulation.

In some embodiments, the permeability enhancer and optional enteric coating are those disclosed in U.S. Pat. No. 9,579,383 (Holmes et al., issued Feb. 28, 2017), which is incorporated herein by reference in its entirety.

Derivatives, Prodrugs, and Stereoisomers of Niclosamide

Derivatives of the parent niclosamide molecule that retain niclosamide activity, such as anti-coronavirus activity (the same activity, or different in type or extent), can be utilized.

Derivatives of niclosamide can be synthesized by chemical transformations of the compounds' functional groups using standard chemical reactions. For example, these standard chemical reactions can include, but are not limited to: polar reactions under basic conditions, polar reactions under acidic conditions, pericyclic reactions, and free radical reactions. In another example, these standard chemical reactions can include, but are not limited to: addition reactions, substitution reactions, oxidation reactions, reduction reactions, elimination reactions, hydrolysis, acylation, amidations, etherification, and esterification. Alkane functional group transformations can include, but are not limited to: free radical chlorination (hv, $Cl_2$), free radical bromination (hv, $Br_2$), and allylic bromination (NBS). Alkene functional group transformations can include, but are not limited to: addition of HCl, addition of HBr, addition of HI, addition of $H_3O(+)$, chlorination ($Cl_2$) bromination ($Br_2$), iodination ($I_2$), chlorohydrin formation ($Cl_2/H_2O$), bromohydrin formation ($Br_2/H_2O$), ether formation ($H^+/ROH$), oxymercuration ($Hg(OAc)_2/H_2O$), oxymercuration, ($Hg(OAc)_2/ROH$), hydroboration, epoxidation ($RCO_3H$), dihydroxylation ($OsO_4$), dihydroxylation ($KMnO_4$), cyclopropanation, dichlorocyclopropanation, ozonolysis (reductive workup), ozonolysis (oxidative workup), oxidative cleavage ($KMnO_4$), hydrogenation, rearrangements (H shift), rearrangements (alkyl shift), free radical addition of HBr, and Sharpless epoxidation. Alkyne functional group transformations can include, but are not limited to: deprotonation (acetylide formation), $S_N2$ with alkyl halides, partial reduction (Lindlar), partial, reduction ($Na/NH_3$), hydroboration, oxymercuration, addition of HCl, HBr, or HI, addition of HCl, HBr, or HI, hydrogenation, ozonolysis, oxidative cleavage ($KMnO_4$), and halogenation ($Cl_2$, $Br_2$, $I_2$). The substitution reaction can include, but is not limited to: alcohol formation, nitrile formation, thiol formation, ether formation, thioether formation, azides, ester formation, acetylide addition, alkanes (Gilman reagents), ammonium salt formation, alkyl chloride formation, alkyl bromide formation, alkyl iodide formation, alkyl shift, and hydride shift. Elimination reactions can include, but are not limited to: alkenes from alkyl halides, alkenes from alcohols (strong acid), alkenes from alcohols ($POCl_3$), alkenes from alkyl halides, E1 with rearrangement (alkyl shift), Hoffmann elimination, and alkyne formation via elimination E1 with rearrangement (hydride shift). Organometallic reactions can include, but are not limited to: Grignard formation (alkyl halides), Grignard formation (alkenyl halides), reaction of Grignards with acids, addition of Grignards to aldehydes, addition of Grignards to ketones, addition of Grignards to esters, reaction of Grignards with $CO_2$, addition of Grignards to nitriles, formation of organolithium reagents, formation of Gilman reagents, $S_N2$ with Gilman reagents, addition of Gilman reagents to enones, addition of Gilman to acyl halides, Heck reaction, Suzuki reaction, and Stille reaction. Reactions of epoxides can include, but are not limited to: epoxide opening (basic conditions), epoxide opening (acidic conditions), epoxide opening (diol formation), epoxide formation (from halohydrins), epoxide formation (from alkenes), and Sharpless epoxidation of alkenes. Reactions of alcohols and thiols can include, but are not limited to: deprotonation (alkoxide formation), protonation (onium ion formation), conversion to tosylates/mesylates, conversion to alkyl chlorides ($SOCl_2$), conversion to alkyl bromides ($PBr_3$), oxidation to aldehydes (PCC), oxidation to ketones (PCC+others), oxidation to carboxylic acid, ($H_2CrO_4$+others), protection as silyl ethers, thiol formation ($S_N2$), and thiol oxidation to disulfides. Reactions of dienes can include, but are not limited to: Diels-alder reaction, polymerization of dienes, reactions of aromatics (arenes), nitration ($HNO_3/H_2SO_4$), chlorination ($Cl_2$ plus catalyst), bromination ($Br_2$ plus catalyst), sulfonylation ($SO_3/H_2SO_4$), Friedel Crafts alkylation (R-X plus catalyst), Friedel Crafts acylation (RCOX plus catalyst), iodination ($I_2$/catalyst), Side chain oxidation ($KMnO_4$), reduction of nitro groups, reduction of aromatic ketones, Side chain bromination, nucleophilic aromatic substitution ($S_NAr$), and aryne formation ($S_NAr$ via arynes). Reactions of aldehydes and ketones can include, but are not limited to: hydrate formation ($H_2O$), cyanohydrin formation (CN), reduction of aldehydes ($NaBH_4$), reduction of aldehydes ($LiAlH_4$), reduction of ketones ($NaBH_4$), reduction of ketones ($LiAlH_4$), Grignard addition to aldehydes, Grignard addition to ketones, acetal formation ($ROH/H^+$), acetal hydrolysis ($H_3O^+$), imine, formation ($RNH_2$), Enamine formation ($R_2NH$), Wolff-Kishner: reduction to alkanes, Clemmensen, reduction to alkanes, oxidation to carboxylic acid ($H_2CrO_4$ or $KMnO_4$), keto-enol tautomerism, enolate formation, aldol addition reaction, alkylation of enolates, Wittig reaction (alkene formation), thioacetal formation, imine hydrolysis, oxidation to carboxylic acids (Tollens), haloform reaction, Baeyer-Villiger reaction, aldol condensation, Cannizarro reaction. Reactions of carboxylic acids can include, but are not limited to: deprotonation (carboxylate formation), formation via Grignard and $CO_2$, conversion to acid chloride ($SOCl_2$), reduction ($LiAlH_4$), Fischer esterification, and decarboxylation (of β-keto acids). Reactions of esters can include, but are not limited to: reduction to aldehydes (DIBAL-H), reduction to alcohols ($LiAlH_4$), hydrolysis to carboxylic acid (acidic), hydrolysis to carboxylic acid (basic), addition of Grignard reagents to esters, Claisen condensation, and transesterification (basic conditions). Reactions of acyl halides can include, but are not limited to: conversion to esters (ROH), conversion to carboxylic acids ($H_2O$), conversion to anhydrides ($RCO_2$), conversion to amides ($RNH_2$), conversion to ketones (Gilman reagents), and conversion to aldehydes ($LiAlH(OtBu)_3$). Reactions of α,β-unsaturated ketones (enones) can include, but are not limited to: Michael reaction (conjugate addition of enolates), conjugate addition of Gilman reagents, conjugate addition of other nucleophiles. Reactions of amines and amides can include, but are not limited to: dehydration of amides to nitriles ($P_2O_5$), Hofmann rearrangement, Gabriel synthesis of amines, reductive amination, formation of diazonium salts, reactions of diazonium salts, amide formation using DCC, amide formation from acid halides, and Curtius rearrangement. Reactions of nitriles can include, but are not limited to: addition of Grignard reagents to nitriles, reduction to amines ($LiAlH_4$), hydrolysis to carboxylic acids. Optionally, potential derivatives of niclosamide can be tested for the ability to inhibit cell entry, cytotoxicity, viral replication, virus yield, and infection using other methods known in the art.

The niclosamide compound may be: (a) niclosamide, (b) a niclosamide derivative, (c) a metabolite or prodrug of (a) or (b), or (d) a pharmaceutically acceptable salt of (a), (b), or (c). In some embodiments, the niclosamide or niclosamide derivative has a structure of FIG. 9A, FIG. 9B, FIG. 9C, or FIG. 9D (Formula 1, Formula 2, Formula 3, or Formula 4, respectively).

In some embodiments, the niclosamide or niclosamide derivative has a structure of FIG. 1A (Formula 1):

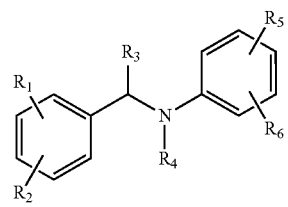

Formula 1, or a pharmaceutically acceptable salt thereof, where $R_1$, $R_2$, $R_3$, $R_4$, $R_5$, $R_6$ can be independently selected from the group consisting of a H; F; Cl; Br; I; OH; ketone (=O); ($C_{1-6}$)alkyl, such as methyl, ethyl, n-propyl, isopropyl, n-butyl, sec-butyl, isobutyl, tert-butyl; ($C_{2-6}$)alkenyl, such as ethenyl, propenyl, butenyl, where the double bond can be located at any position in the alkenyl carbon chain, including any alkenyl conformational isomers; ($C_{2-6}$)alkynyl, where the triple bond can be located at any position in the alkenyl carbon chain, including any alkynyl conformational isomers; ether [—OR, where R can include $(C_{1-6})$ alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X can include F, Cl, Br, and I]; carbonyl [—COR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aldehyde (—CHO); ester [—OC(=O)R, —ROC(=O)R', RC(=O)OR', —C(=O)OR', where R and R' can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers]; carbonate ester [—OCOOR, where R can include $(C_{1-6})$alkyl, such as methyl, ethyl, n-propyl, isopropyl, n-butyl, sec-butyl, isobutyl, tert-butyl; and $(C_{1-6})$alkenyl, such as ethenyl, propenyl, butenyl, where the double bond can be located at any position in the alkenyl carbon chain, including any alkenyl conformational isomers]; carboxyl (—COOH); amide [—CONR'R", where R' and R" can be independently selected from hydrogen; alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, including any alkenyl conformational isomers]; amines [—NR'R", where R' and R" can be independently selected from hydrogen; $(C_{1-6})$ alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; borono and boronate [—B(OR')(R"), where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; borinate [—B(R')(OR"), where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosophino [—PR$_2$, where R can include hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers; phosphate [—OP(=O)(OR)$_2$, where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers; phosphono [—RP(=O)(OH), where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; thiol (—SH); thioalkyl; alkylthio; sulfide [—SR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; disulfide [—SSR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers], sulfonamide; sulfinyl [—S(=O)R, where R can include $(C_{1-6})$ alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; sulfino (—SO$_2$H); sulfo (—SO$_3$H); thiocyanate; isothiocyanate; carbonothioyl [—C(=S)R where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers];

where $R_2$ and $R_4$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$ alkane ring and/or $(C_{2-8})$alkene ring, such as a five-membered ring or a six-membered ring; and where $R_4$ and $R_6$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$ alkane ring and/or $(C_{2-8})$alkene ring, such as a five-membered ring or a six-membered ring.

Figure 1B:
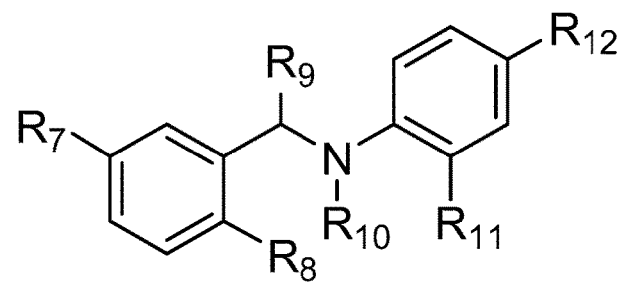

In some embodiments, the niclosamide or niclosamide derivative has the structure of FIG. 1B (Formula 2):

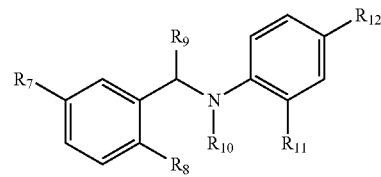

Formula 2, or a pharmaceutically acceptable salt thereof, where $R_7$, $R_8$, $R_9$, $R_{10}$, $R_{11}$, $R_{12}$ can be independently selected from the group consisting of a H; F; Cl; Br; I; OH; ketone (=O); $(C_{1-6})$alkyl, such as methyl, ethyl, n-propyl, isopropyl, n-butyl, sec-butyl, isobutyl, tert-butyl; $(C_{2-6})$alkenyl, such as ethenyl, propenyl, butenyl, where the double bond can be located at any position in the alkenyl carbon chain, including any alkenyl conformational isomers; $(C_{2-6})$alkynyl, where the triple bond can be located at any position in the alkynyl carbon chain, including any alkynyl conformational isomers; ether [—OR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X can include F, Cl, Br, and I]; carbonyl [—COR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aldehyde (—CHO); ester [—OC(=O)R, —ROC(=O)R', RC(=O)OR', —C(=O)OR', where R and R' can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers]; carbonate ester [—OCOOR, where R can include $(C_{1-6})$alkyl, such as methyl, ethyl, n-propyl, isopropyl, n-butyl, sec-butyl, isobutyl, tert-butyl; and $(C_{1-6})$alkenyl, such as ethenyl, propenyl, butenyl, where the double bond can be located at any position in the alkenyl carbon chain, including any alkenyl conformational isomers]; carboxyl (—COOH); amide [—CONR'R", where R' and R" can be independently selected from hydrogen; alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, including any alkenyl conformational isomers]; amines [—NR'R", where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; borono and boronate [—B(OR')(R"), where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; borinate [—B(R')(OR"), where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosophino [—PR$_2$, where R can include hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosphate [—OP(=O)(OR)$_2$, where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers; phosphono [—RP(=O)(OH), where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; thiol (—SH); thioalkyl; alkylthio; sulfide [—SR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; disulfide [—SSR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers], sulfonamide; sulfinyl [—S(=O)R, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; sulfino (—SO$_2$H); sulfo (—SO$_3$H); thiocyanate; isothiocyanate; carbonothioyl [—C(=S)R where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers];

where $R_7$ and $R_{10}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$ alkane ring and/or $(C_{2-8})$alkene ring, such as a five-membered ring or a six-membered ring;

where $R_8$ and $R_{10}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$ alkane ring and/or $(C_{2-8})$alkene ring, such as a five-membered ring or a six-membered ring; and where $R_{10}$ and $R_{11}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$ alkane ring and/or $(C_{2-8})$alkene ring, such as a five-membered ring or a six-membered ring.

Figure 1C:
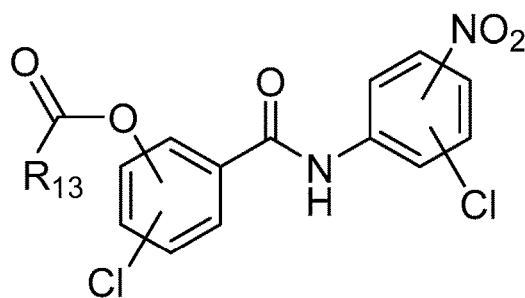

In some embodiments, the niclosamide or niclosamide derivative has the structure of FIG. 1C (Formula 3):

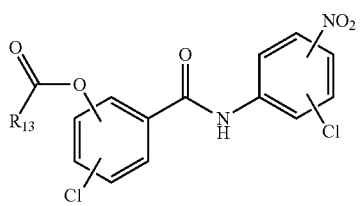

Formula 3, or a pharmaceutically acceptable salt thereof, where $R_{13}$ can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers.

Figure 1D:
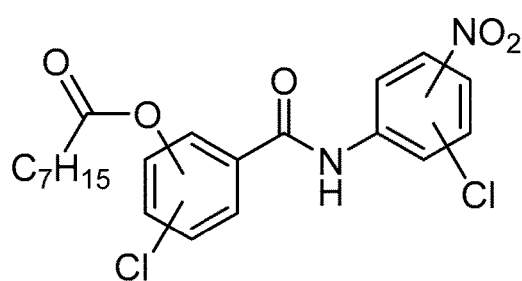

In some embodiments, the niclosamide or niclosamide derivative has the structure of FIG. 1D (Formula 4):

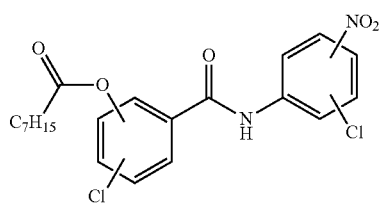

Formula 4, or a pharmaceutically acceptable salt thereof.

In some embodiments, the niclosamide compound is a derivative of niclosamide such as p-niclosamide (Pan J-X et al., "Niclosamide, an antihelminthic agent, demonstrates antitumor activity by blocking multiple signaling pathways of cancer stem cells," *Chin J Cancer*, 2012, 31(4):178-18448), which is incorporated herein by reference in its entirety, or an acyl derivative of niclosamide, such as DK-520 (Mook R A et al., Structure-activity studies of Wnt/β-catenin inhibition in the Niclosamide chemotype: Identification of derivatives with improved drug exposure. *Bioorg Med Chem.*;23(17):5829-38 (2015)), which is incorporated herein by reference in its entirety, or a pharmaceutically acceptable salt of these compounds.

In some embodiments, the niclosamide compound is a derivative of niclosamide and is one or a combination of analogs described in Shamim K et al., "Application of niclosamide and analogs as small molecule inhibitors of Zika virus and SARS-CoV-2 infection," *Bioorg Med Chem Lett.*, 2021 May 15; 40: 127906, which is incorporated herein by reference in its entirety, or a pharmaceutically acceptable salt of these compounds.

In some embodiments, the niclosamide compound is a derivative of niclosamide and is one or a combination of derivatives described in Tang Z et al., "Structure-Activity Relationship of Niclosamide Derivatives", *Anticancer Research*, June 2017, 37 (6) 2839-2843, which is incorporated herein by reference in its entirety, or a pharmaceutically acceptable salt of these compounds.

In some embodiments, the niclosamide compound is one or a combination of O-alkylamino-tethered derivative described in Chen H et al., "Discovery of O-alkylamino-tethered niclosamide derivatives as potent and orally bioavailable anticancer agents," *ACS Med. Chem. Lett.*, 2013, 4:180-185, which is incorporated herein by reference in its entirety, or a pharmaceutically acceptable salt of these compounds.

Compositions and Treatment

The niclosamide compounds can be formulated into pharmaceutically acceptable salt forms or hydrate forms. Pharmaceutically acceptable salt forms include the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically acceptable base addition salts include sodium, potassium, calcium, ammonium, and magnesium salts.

Administration of the composition can be carried out in the form of an oral tablet, capsule, or liquid formulation containing a therapeutically effective amount of the active ingredient (one or more niclosamide compounds). Administration is not limited to oral delivery and includes intravascular (e.g., intravenous), intramuscular, or another means known in the pharmaceutical art for administration of active pharmaceutical ingredients.

Therapeutic or prophylactic application of the compositions can be accomplished by any suitable therapeutic or prophylactic method and technique presently or prospectively known to those skilled in the art. The compositions can be administered by any suitable route known in the art including, for example, oral, intramuscular, intraspinal, intracranial, nasal, rectal, parenteral, subcutaneous, or intravascular (e.g., intravenous) routes of administration. Administration of the compositions can be continuous or at distinct intervals as can be readily determined by a person skilled in the art.

In some embodiments, an amount of niclosamide compound (e.g., 100 mg-1,000 mg) is to be administered 1, 2, 3, 4, or times per day, for 1, 2, 3, 4, 5, 6, 7, or more days. Treatment can continue as needed, e.g., for several weeks. Optionally, the treatment regimen can include a loading dose, with one or more daily maintenance doses. For example, in some embodiments, an initial loading dose in the range of 100 mg to 1,000 is administered, followed by a maintenance dose in the range of 100 mg to 1,000 mg every 12 hours for 1, 2, 3, 4, 5, 6, or 7, or more days. In some embodiments, an initial loading dose in the range of 200 mg to 600 mg is administered, followed by a maintenance dose in the range of 100 mg to 300 mg every 12 hours for a total of 9 doses.

Niclosamide compounds and compositions comprising them can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive inhibitor is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, softgels, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject inhibitors include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the inhibitors can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the inhibitor based on the weight of the total composition including carrier or diluent.

The compositions of the subject invention can also be administered utilizing liposome technology, slow release capsules, implantable pumps, and biodegradable containers. These delivery methods can, advantageously, provide a uniform dosage over an extended period of time.

The subject invention also concerns a packaged dosage formulation comprising in one or more packages, packets, or containers at least one niclosamide compound and at least one permeability enhancer formulated in a pharmaceutically acceptable dosage. The package can contain discrete quantities of the dosage formulation, such as tablet, capsules, lozenge, and powders. The quantity of niclosamide compound in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg. In some embodiments, the amount is in the range of 100 mg to 600 mg, to be administered 1, 2, 3, or 4 times per day, for 2, 3, 4, 5, 6, 7 or more days.

The subject invention also concerns kits comprising in one or more containers at least one niclosamide compound and at least one permeability enhancer. A kit of the invention can also comprise one or more compounds, biological molecules, or drugs. In one embodiment, a kit of the invention further comprises one or more of a drug or composition used in treating a viral infection (e.g., human coronavirus, such as SARS-CoV-2).

Optionally, the methods further comprise, prior to administering the composition to the subject, identifying the subject as having a human coronavirus infection (human coronavirus, generally, or a specific strain of coronavirus, such as SARS-CoV-2), or not having a human coronavirus infection. If the subject is identified as having a human coronavirus infection, the composition can be administered to the human subject as therapy. If the human subject is identified as not having a human coronavirus infection, the composition can be withheld, or the composition can be administered as prophylaxis, or an alternative agent can be given. The identifying step may comprise assaying a biological sample (e.g., blood, saliva, or urine) obtained from the subject for the presence of human coronavirus nucleic acids or human coronavirus proteins, such as SARS-CoV-2 nucleic acids or proteins. In some embodiments, assaying includes the use of reverse transcriptase-polymerase chain reaction (RT-PCR), immunological assay (e.g., ELISA), or Plaque-reduction neutralization testing (PRNT).

Thus, optionally, the methods include, prior to administration of the composition, or re-administration of the composition, determining whether the subject has a human coronavirus infection or one or more symptoms consistent with a human coronavirus infection. Some individuals infected with coronavirus will not know they have the infection because they will not have symptoms (i.e., are asymptomatic).

In some embodiments of the methods of the invention, the human coronavirus is SARS-CoV-2, or a variant of SARS-CoV-2, such as the B.1.1.7 variant, B.1.351 variant, P.1 variant, B.1.427 variant, and B.1.429 variant.

SARS-CoV-2 is a novel human coronavirus that causes coronavirus disease 2019, also known as COVID-19 and COVID19.

SARS-CoV-2 has multiple variants currently circulating globally. Such SARS-CoV-2 variants include at least B.1.1.7 identified in the United Kingdom, B.1.351 identified in South Africa, and P.1 identified in travelers from Brazil. For example, SARS-CoV-2 variants may include mutations, such as the following: E484K, which was first discovered in the United Kingdom; L452R, which was detected in Denmark; and D614G discovered in China in January 2020.

In some embodiments of the methods of the invention, the human coronavirus is selected from among SARS-CoV-2, SARS-CoV, and MERS-CoV. SARS-CoV-2 is a novel human coronavirus that causes coronavirus disease 2019, also known as COVID-19 and COVID19. MERS-CoV is the beta coronavirus that causes Middle East Respiratory Syndrome, or MERS. SARS-CoV is the beta coronavirus that causes severe acute respiratory syndrome, or SARS.

In some embodiments of the methods of the invention, the human coronavirus is a common human coronavirus, such as type 229E (an alpha coronavirus), NL63 (an alpha coronavirus), OC43 (a beta coronavirus), and HKU1 (a beta coronavirus).

The symptoms of a coronavirus infection (if the subject is not asymptomatic) depend on the type of coronavirus and severity of the infection. If a subject has a mild to moderate upper-respiratory infection, such as the common cold, symptoms may include: runny nose, headache, cough, sore throat, fever, and general feeling of being unwell. Some coronaviruses can cause severe symptoms. These infections may turn into bronchitis and pneumonia, which can cause symptoms such as fever (which can be quite high with pneumonia), cough with mucus, shortness of breath, and chest pain or tightness when the subject breaths or coughs.

The clinical spectrum of SARS-CoV-2 may range from mild disease with non-specific signs and symptoms of acute respiratory illness, to severe pneumonia with respiratory failure and septic shock. Asymptomatic infections have also been reported.

To diagnose coronavirus infections, healthcare providers typically take the subject's medical history and ask the subject their symptoms, do a physical examination, and may conduct laboratory tests on a biological sample such as blood, or a respiratory specimen such as sputum or a throat swab.

In some embodiments, a molecular assay may be used to detect the presence or absence of human coronavirus in a biological sample from the subject. For example, several assays that detect SARS-CoV-2 have been under development. Some assays may detect only the novel virus and some may also detect other strains (e.g., SARS-CoV) that are genetically similar. The table below is a summary of some available protocols and their gene targets.

| Country | Institution | Gene targets |
| --- | --- | --- |
| United States | US CDC | Three N primers, RdRP |
| China | China CDC | ORF1ab and N |
| Germany | Charite' | RdRP, E, N |
| Hong Kong | HKU | ORF1b-nsp14, N |
| Japan | National Institute of Infection Diseases, Department of Virology III | Pancorona and multiple targets, Spike protein |
| Thailand | National Institute of Health | N |

China CDC Primers and probes for detection 2019-nCoV (24 Jan. 2020)

Diagnostic detection of Wuhan coronavirus 2019 by real-time RT-PCR—Charité, Berlin Germany (17 Jan. 2020)

Detection of 2019 novel coronavirus (2019-nCoV) in suspected human cases by RT-PCR—Hong Kong University (23 Jan. 2020)

PCR and sequencing protocol for 2019-nCoV—Department of Medical Sciences, Ministry of Public Health, Thailand (Updated 28 Jan. 2020)

PCR and sequencing protocols for 2019-nCoV—National Institute of Infectious Diseases Japan (24 Jan. 2020)

US CDC Real-Time RT-PCR Panel for Detection 2019-Novel Coronavirus (28 Jan. 2020)

US CDC panel primer and probes—U.S. CDC, USA (28 Jan. 2020)

("WHO interim guidance for laboratory testing for 2019 novel coronavirus (2019-nCoV) in humans" from World Health Organization website).

SARS-CoV-2 RNA has been detected from upper and lower respiratory tract specimens, and the virus has been isolated from upper respiratory tract specimens and bronchoalveolar lavage fluid. SARS-CoV-2 RNA has been detected in blood and stool specimens. The duration of SARS-CoV-2 RNA detection in the upper and lower respiratory tracts and in extrapulmonary specimens has not been determined. It is possible that RNA could be detected for weeks, which has occurred in some cases of MERS-CoV or SARS-CoV infection. Viable SARS-CoV has been isolated from respiratory, blood, urine, and stool specimens, and viable MERS-CoV has been isolated from respiratory tract specimens.

The compositions of the invention may include additional bioactive agents, and the methods of the invention may include contacting the cell with additional agents and administering additional bioactive agents to the subject. For example, in the case of coronavirus such as SARS-CoV-2 and variants thereof, one or more additional agents that have, or may have, activity against the virus or its signs or symptoms may be used before, simultaneously with, or after the compositions of the invention. Examples of such agents include, but are not limited to, remdesivir, hydroxychloroquine, chloroquine, favipiravir, lopinivar or ritonavir with or without interferon beta-la, sarilumab, combination of ASC-09 and ritonavir, tocilizumab, lenzilumab, dapaglifozin, CD24Fc, convalescent plasma or hyperimmune serum, casirivimab and/or imdevimab, and bamlanivimab and/or etesevimab. A list of bioactive agents from natural compounds that may be used is provided in Table 1 of Prasansuklab A et al., "Anti-COVID-19 drug candidates: A review on potential biological activities of natural products in the management of new coronavirus infection", *Journal of Traditional and Complementary Medicine*, 2021, 11:144-157, which is incorporated herein by reference in its entirety.

Treatment methods for coronavirus infection optionally include steps of advising that the subject get plenty of rest and drink fluids for hydration and administration of agents that alleviate symptoms of coronavirus infection, such as those that reduce fever and pain (e.g., acetaminophen and/or paracetamol), particularly for common human coronavirus infections. The methods may include administration of the fluids to the subject for hydration.

Optionally, the subject may be administered one or more of the following before, during, and/or after administration of the composition: acetaminophen (e.g., 500 mg upon need), vitamin C (e.g., 1000 mg twice/day), zinc (e.g., 75-125 mg/day), vitamin D3 (e.g., 5000 IU/day), azithromycin (e.g., 250 mg/day for 5 days), oxygen therapy/C-Pap if needed, dexamethasone (e.g., 6 mg/day), methylprednisolone (e.g., 40 mg twice per day), or mechanical ventilation, if needed.

The subject may be any age or gender. In some cases, the subject may be an infant or older adult. In some embodiments, the subject is 40 years of age or older. In some embodiments, the subject is 55 years of age or older. In some embodiments, the subject is 60 years of age or older. In some embodiments, the subject is an infant. In some embodiments, the subject (of any age or gender) has heart or lung disease, or a weakened immune system. In some embodiments, the subject is symptomatic at the time of administration of the composition. In other embodiments, the subject is asymptomatic at the time of administration of the composition.

In some embodiments, the subject has cancer at the time of administration of the composition. In other embodiments, the subject does not have cancer at the time of administration of the composition.

The invention further provides kits, including at least one niclosamide compound and at least one permeability enhancers in pharmaceutical formulations, packaged into suitable packaging material, optionally in combination with instructions for using the kit components, e.g., instructions for performing a method of the invention. In one embodiment, a kit includes an amount of at least one niclosamide compound and at least one permeability enhancer, and instructions for administering the composition to a subject in need of treatment on a label or packaging insert. In further embodiments, a kit includes an article of manufacture, for delivering the inhibitor into a subject locally, regionally or systemically, for example.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating a human coronavirus infection, an assay for identifying a subject having a human coronavirus infection, etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, pharmaceutical compositions can be included in a container, pack, or dispenser together with instructions for administration to a subject to treat a human coronavirus infection. Instructions may additionally include appropriate administration route, dosage information, indications of a satisfactory clinical endpoint or any adverse symptoms that may occur, storage information, expiration date, or any information required by regulatory agencies such as the Food and Drug Administration or European Medicines Agency for use in a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing the niclosamide compound. The kit can also include control components for assaying for the presence of human coronavirus, e.g., a control sample or a standard. Each component of the kit can be enclosed within an individual container or in a mixture and all of the various containers can be within single or multiple packages.

DEFINITIONS

As used herein, a subject is "in need of" a treatment if such human subject would benefit biologically, medically or in quality of life from such treatment (preferably, a human). In some embodiments, the subject has a coronavirus infection and is in need of therapy. In other embodiments, the subject does not have a coronavirus infection and is in need of prophylaxis. In some embodiments, the subject in need of prophylaxis is at risk of becoming infected with the coronavirus. In some embodiments, the subject is at increased risk of becoming infected with the coronavirus relative to others in the population.

As used herein, the terms "subject", "patient", and "individual" refer to a human or non-human animal of any age or gender. In some embodiments, the subject is a human or non-human mammal. In some embodiments, the subject is human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: oral, oral, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic.

As used herein, the term "contacting" in the context of contacting a cell with at least one niclosamide compound in vitro or in vivo means bringing at least one niclosamide compound into contact with the cell, or vice-versa, or any other manner of causing the inhibitor and the cell to come into contact. The cell may be a human or non-human animal cell. In some embodiments, the cell is a human or non-human mammalian cell. In some embodiments, the cell is human cell.

The niclosamide compounds and permeability enhancers of the present invention can be formulated into pharmaceutically-acceptable salt forms. Pharmaceutically-acceptable salts of the compounds of the invention can be prepared using conventional techniques. "Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, a "derivative" or "pharmaceutically active derivative" refers to any compound that upon administration to the recipient, is capable of providing directly or indirectly, the activity disclosed herein (e.g., anti-coronavirus activity). The term "indirectly" also encompasses "prodrugs" which may be converted to the active form of the drug, e.g., via endogenous enzymes or metabolism (biotransformation). The prodrug is a derivative of the compounds according to the invention and presenting activity of the parent compound (e.g., coronavirus inhibitory activity) that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g., by oxidation, reduction, hydrolysis or the like, each of which is carried out enzymatically. These compounds can be produced from compounds of the present invention according to well-known methods. The term "indirectly" also encompasses metabolites of compounds according to the invention. Chemical reactions, reactants, and reagents useful for making derivatives can be found, for example, in *March's Advanced Organic Chemistry*, 7th edition, 2013, Michael B. Smith, which is incorporated herein by reference in its entirety.

More specifically, the term "prodrug" refers to a chemical compound that can be converted by the body (i.e., biotransformed) to another chemical compound that has pharmacological activity. The prodrug may itself have pharmacological activity before conversion, or be inactive before conversion and activated upon conversion. Active prodrugs or inactive prodrugs of compounds of the invention may be administered to a subject or contacted with a cell in vitro or in vivo. Instead of administering a drug directly, a prodrug may be used instead to improve how a drug is absorbed, distributed, metabolized, and excreted (ADME). For example, a prodrug may be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastrointestinal fluids or in the circulation system (Wu, Kuei-Meng, "A New Classification of Prodrugs: Regulatory Perspectives, *Pharmaceuticals*, 2009, 2(3):77-81, which is incorporated by reference herein in its entirety).

The term "metabolite" refers to all molecules derived from any of the compounds according to the present invention in a cell or organism, preferably mammal. Pharmaceutically active metabolites of the compounds of the invention may be administered to a subject or contacted with a cell in vitro or in vivo.

The phrase "pharmaceutically acceptable" indicates that the substance or composition must be compatible chemically and/or toxicologically, with the other ingredients comprising a formulation, and/or the mammal being treated therewith.

Pharmaceutical formulations include "pharmaceutically acceptable" and "physiologically acceptable" carriers, diluents or excipients. In this context, the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions.

The phrase "effective amount" means an amount of an agent, such as a niclosamide compound, permeability enhancer, or composition comprising one or both, that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a subject is "in need of" a treatment if such human or non-human animal subject would benefit biologically, medically or in quality of life from such treatment (preferably, a human).

As used herein, the term "inhibit", "inhibition" or "inhibiting" refers to the reduction or suppression of a given condition, symptom, or disorder, or disease (e.g., coronavirus infection, or coronavirus viral load or titer), or a significant decrease in the baseline activity of a biological activity or process.

The terms "compounds of the present invention" or "agents of the invention" (unless specifically identified otherwise) refer to niclosamide compounds and permeability enhancers, including salts thereof, as well as all stereoisomers (including diastereoisomers and enantiomers), rotamers, tautomers and isotopically labeled compounds (including deuterium substitutions), as well as inherently formed moieties (e.g., polymorphs, solvates and/or hydrates). For purposes of this invention, solvates and hydrates are generally considered compositions.

The term "a," "an," "the" and similar terms used in the context of the present invention (especially in the context of the claims) are to be construed to cover both the singular and plural unless otherwise indicated herein or clearly contradicted by the context. For example, the term "cell" includes a singular cell and a plurality of cells unless specified to the contrary; and the term "compound" includes a singular inhibitor and a plurality of compounds.

EXEMPLIFIED EMBODIMENTS

Examples of claimed embodiments of the invention include, but are not limited to:

Embodiment 1. A composition comprising a niclosamide compound and a permeability enhancer, wherein the permeability enhancer increases the amount of the niclosamide compound capable of being transported across a cell membrane.

Embodiment 2. The composition of embodiment 1, wherein the composition increases the amount of the niclosamide compound capable of being transported across a Caco-2 cell membrane by at least 150% relative to the amount capable of being transported across the Caco-2 Cell membrane in the absence of the permeability enhancer.

Embodiment 3. The composition of embodiment 1 or 2, wherein the permeability enhancer is selected from the group consisting of fatty acids, fatty acid esters, fatty acid salts, glycerol, surfactants, cyclodextrins, sodium salicylate, ethylenediamine tetraacetic acid, citric acid, chitosan, chitosan derivatives, N-trimethyl chitosan chloride, monocarboxymethyl-chitosan, palmitoyl carnitine chloride, acyl carnitines, ethylene glycol tetraacetic acid, 3-alkylamido-2- alkoxypropyl-phosphocholine derivatives, alkanoylcholines, N-acetylated amino acids, mucoadhesive polymers, phospholipids, piperine, 1-methylpiperazine, alpha-amino acids, and mineral oil.

Embodiment 4. The composition of embodiment 1, wherein the permeability enhancer is selected from the group consisting of one or more fatty acid esters, glycerol, glycerol monocaprylate, and dimethylpalmityl-ammonio propanesulfonate (PPS).

Embodiment 5. The composition of embodiment 1, wherein the permeability enhancer comprises or consists of glycerol.

Embodiment 6. The composition of embodiment 1, wherein the permeability enhancer comprises or consists of glycerol monocaprylate.

Embodiment 7. The composition of embodiment 1, wherein the permeability enhancer comprises or consists of dimethylpalmityl-ammonio propanesulfonate.

Embodiment 8. The composition of embodiment 1, wherein the niclosamide compound is niclosamide or a pharmaceutically acceptable salt thereof.

Embodiment 9. The composition of embodiment 1, wherein the niclosamide compound and the permeability enhancer form a mixture that is emulsified.

Embodiment 10. The composition of any preceding embodiment, wherein the composition further comprises an enteric- or pH-sensitive coating or layer surrounding the composition.

Embodiment 11. The composition of embodiment 10, wherein the composition has an enteric coating surrounding the composition.

Embodiment 12. The composition of embodiment 11, wherein the enteric coating comprises one or more enteric polymers selected from among: cellulose acetate phthalate, cellulose acetate trimellitate, hydroxypropyl methylcellulose acetate succinate, hydroxypropyl methylcellulose phthalate, and polyvinyl acetate phthalate; and anionic polymer based on methacrylic acid and methacrylic acid esters.

Embodiment 13. An oral dosage form comprising the composition of any preceding embodiment, wherein the composition comprises a therapeutically effective amount of the niclosamide compound and a permeability-enhancing amount of a permeability enhancer.

Embodiment 14. The oral dosage form of embodiment 13, wherein the permeability enhancer is one or more selected from among: glycerol, glycerol monocaprylate, and dimethylpalmityl-ammonio propanesulfonate (PPS).

Embodiment 15. The oral dosage form of embodiment 13 or 14, wherein the permeability enhancer is a cyclodextrin and the niclosamide is complexed with the cyclodextrin.

Embodiment 16. The oral dosage form of any preceding embodiment, wherein the niclosamide compound and the permeability enhancer form a mixture that is emulsified.

Embodiment 17. The oral dosage form of any preceding embodiment, wherein the permeability enhancer is present in the composition at a concentration from about 5% to about 95% of the combined weight of the niclosamide compound and the permeability enhancer.

Embodiment 18. The oral dosage form of any preceding embodiment, further comprising an enteric- or pH-sensitive coating or layer surrounding the composition.

Embodiment 19. The oral dosage form of embodiment 18, wherein the composition has an enteric coating surrounding the composition.

Embodiment 20. The oral dosage form of embodiment 19, wherein the enteric coating comprises one or more enteric polymers selected from among: cellulose acetate phthalate, cellulose acetate trimellitate, hydroxypropyl methylcellulose acetate succinate, hydroxypropyl methylcellulose phthalate, and polyvinyl acetate phthalate; and anionic polymer based on methacrylic acid and methacrylic acid esters.

Embodiment 21. The oral dosage form of any preceding embodiment, wherein the oral dosage form is a solid oral dosage form selected from among a table, capsule, sachet, powder, granules, or orally dispersible film.

Embodiment 22. The oral dosage form of any one of embodiments 13 to 20, wherein the oral dosage form is a liquid oral dosage forms or semi-solid selected from among a syrup, solution, ampoule, dispersion, or softgel.

Embodiment 23. A method for treating or preventing human coronavirus infection, or a symptom thereof, in a human subject, said method comprising administering an effective amount of a composition or oral dosage form of any preceding embodiment to the human subject.

Embodiment 24. The method of embodiment 23, wherein the coronavirus is SARS-CoV-2, or a variant thereof (e.g., the B.1.1.7 variant, B.1.351 variant, P.1 variant, B.1.427 variant, and B.1.429 variant).

Embodiment 25. The method of embodiment 23, wherein the coronavirus is SARS-CoV.

Embodiment 26. The method of embodiment 23, wherein the coronavirus is MERS-CoV.

Embodiment 27. The method of embodiment 23, wherein the human coronavirus is a common human coronavirus from among 229E, NL63, OC43, and HKU1.

Embodiment 28. The method of any preceding embodiment, wherein the human subject has the coronavirus infection at the time of said administering.

Embodiment 29. The method of embodiment 28, further comprising, prior to said administering, identifying the subject as having the coronavirus infection, wherein said identifying comprises assaying a biological sample obtained from the subject for the presence of coronavirus nucleic acid or coronavirus protein.

Embodiment 30. The method of any one of embodiments 20 to 27, wherein the human subject does not have the coronavirus infection at the time of said administering, and the composition is administered as prophylaxis.

Embodiment 31. The method of any preceding embodiment, wherein the composition is administered orally, intravascularly, nasally, rectally, parenterally, subcutaneously, or intramuscularly.

Embodiment 32. The method of any preceding embodiment, wherein the composition is administered orally or intravenously.

Embodiment 33. The method of any preceding embodiment, wherein the composition is administered orally.

Embodiment 34. The method of any preceding embodiment, further comprising administering another agent for treating or preventing coronavirus infection, or a symptom thereof, in the same formulation as the niclosamide compound and permeability enhancer, or in a separate formulation before, during, or after administration of the niclosamide compound and permeability enhancer.

Embodiment 35. A method for inhibiting a human coronavirus infection in a human cell, comprising contacting the infected human cell with the composition or oral dosage form of any preceding embodiment in vitro or in vivo.

Embodiment 36. The method of embodiment 35, wherein the human coronavirus is selected from among SARS-CoV-2, SARS-CoV, MERS-CoV, 229E, NL63, OC43, and HKU1.

Embodiment 37. The method of embodiment 35, wherein the human coronavirus is SARS-CoV-2, or a variant thereof (or a variant thereof (e.g., the B.1.1.7 variant, B.1.351 variant, P.1 variant, B.1.427 variant, and B.1.429 variant).

Embodiment 38. The method of any one of embodiments 35 to 37, wherein the cell is contacted with the composition in vitro or in vivo prior to infection.

Embodiment 39. The method of any one of embodiments 35 to 37, wherein the cell is contacted with the composition in vitro or in vivo after infection.

Embodiment 40. A composition of matter, comprising:
(a) packaged dosage formulation comprising at least one niclosamide compound and at least one permeability enhancer, in a pharmaceutically acceptable dosage in one or more packages, packets, or containers; and instructions for administering the niclosamide compound to treat or prevent human coronavirus infection; or
(b) a kit comprising, in one or more containers, at least one niclosamide compound and at least one permeability enhancer; and instructions for administering the niclosamide compound to treat or prevent human coronavirus infection.

Embodiment 41. The composition of matter of embodiment 40, wherein the kit further comprises a component for testing for the presence of a human coronavirus infection (e.g., coronavirus nucleic acid or protein) in a biological sample.

Embodiment 42. The composition of matter of embodiment 40 or 41, wherein at least one niclosamide compound and at least one permeability enhancer are in the form of a composition of any preceding embodiment or an oral dosage form of any preceding embodiment.

Embodiment 43. A composition of matter, comprising:
(a) composition comprising a niclosamide compound and a permeability enhancer, wherein the permeability enhancer increases the amount of the niclosamide compound capable of being transported across a cell membrane; or
(b) an oral dosage form comprising the composition of (a), wherein the composition comprises a therapeutically effective amount of the niclosamide compound and a permeability-enhancing amount of the permeability enhancer; or
(c) packaged dosage formulation comprising at least one niclosamide compound and at least one permeability enhancer, in a pharmaceutically acceptable dosage in one or more packages, packets, or containers; and instructions for administering the niclosamide compound to treat or prevent human coronavirus infection, wherein the permeability enhancer increases the amount of the niclosamide compound capable of being transported across a cell membrane; or
(d) a kit comprising, in one or more containers, at least one niclosamide compound and at least one permeability enhancer; and instructions for administering the niclosamide compound to treat or prevent human coronavirus infection, wherein the permeability enhancer increases the amount of the niclosamide compound capable of being transported across a cell membrane.

Embodiment 44. A method for delivering a niclosamide compound to a human or non-human animal subject, comprising administering an effective amount of the composition of (a) or oral dosage form of (b) of embodiment 43 to the human subject.

Embodiment 45. A method for delivering a niclosamide compound to a human or non-human animal cell, comprising contacting a human or non-human animal cell with the composition of (a) or oral dosage form of (b) of embodiment 43 in vitro or in vivo.

All patents, patent applications, provisional applications, and publications referred to or cited herein are incorporated by reference in their entirety, including all figures and tables, to the extent they are not inconsistent with the explicit teachings of this specification.

The following examples are provided to describe the invention in greater detail. The examples are intended illustrate, not to limit, the invention.

Example 1— Evaluation of Various Permeability Enhancers on Caco-2 Permeability of Niclosamide Compound (Prophetic)

Permeability enhancers such as glycerol (e.g., glycerol monocaprylate), dimethylpalmityl-ammonio propanesulfonate (PPS), and cyclodextrin are each mixed with niclosamide or a niclosamide derivative and vortexed and sonicated. For example, the permeability enhancer can be mixed with the niclosamide compound in amounts such that the weight ratio of permeation enhancer to niclosamide ratio is in a desired range, and is subsequently diluted in Hank's Balanced Salt Solution (HBSS, available from Mediatech, Inc., Herndon, Va.) to a level in which the niclosamide compound is present at a desired predetermined concentration (e.g., X μg/mL or X %) and the permeability enhancer concentration of the sample is in a desired predetermined range (e.g., %). Mixing can be conducted by sonication using a bath or probe sonicator, which will convert the relatively low viscosity liquid mixture to a more viscous or paste-like composition that is stable and non-separating.

In like manner, other enhancer compounds are mixed with the niclosamide compound in amounts such that the weight ratio of enhancer to niclosamide compound is in the ranges desired for evaluation, and, similarly, such that when the mixture is subsequently diluted to a level at which the niclosamide compound is present at a desired predetermined concentration (e.g., X μg/mL or X %), and the permeability enhancer concentration of the sample within a desired predetermined range for comparison.

To evaluate the effectiveness of permeability enhancers, data is obtained to demonstrate the ability of one or more permeability enhancer compound(s) to increase niclosamide compound permeability using Caco-2 cell permeability assays. The assays may be performed according to the methods described by Artursson P, Palm K, Luthman K., "Caco-2 Monolayers in Experimental and Theoretical Predictions of Drug Transport", *Adv Drug Deliv Rev.*, 2001 Mar. 1; 46(1-3):27-43, and by Shah P, Jogani V, Bagchi T, Misra A., "Role of Caco-2 Cell Monolayers in Prediction of Intestinal Drug Absorption", *Biotechnol Prog.*, 2006 January-February; 22(1):186-98. Assays are conducted by seeding approximately 68,000 viable Caco-2 cells in 1.12 $cm^2$ Costar Transwell inserts (12-well format, 0.4 micron pore size PET membranes) in Dulbecco's Modified Eagles Medium (high glucose) supplemented with 20% fetal bovine serum, glutamine, pyruvate, non-essential amino acids, epidermal growth factor, ITS (insulin, transferrin, selenium), and penicillin/streptomycin. The cells are incubated for 21-25 days with medium changes every 2-3 days. Transepithelial electrical resistance (TEER) readings are conducted to test the quality of the cell monolayer on the Transwell membrane. The membranes can be washed in HBSS and the resistance across the membrane is measured. Wells having TEER readings of 200Ω cm$^2$ or higher may be used in the permeability assays.

Assays are conducted by washing the transwell inserts containing a Caco-2 cell monolayer in HBSS and placing them in 12-well plates with 1.5 ml of HBSS in the lower well. The niclosamide compound-containing test formulation is diluted into HBSS to provide a desired niclosamide compound concentration (e.g., X μg/mL), and a volume of the solution (e.g., 0.5 ml) is added to the transwell insert. Each formulation is tested in triplicate. The transwell inserts are incubated in a 37° C. incubator with rotation at 50 rpm for 30 minutes. At the end of this period, the transwell inserts are placed in fresh 1.5 ml of HBSS in a new well of the 12-well plate and incubated for an additional 30 minutes. A total of 8 to 10 thirty-minute time points are collected by sequentially moving the transwell inserts to fresh 1.5 ml HBSS in successive wells of the 12-well plates. The amount of niclosamide compound transported into the lower wells is quantitated by LC-MS to define the rate of niclosamide compound transported across the membrane for each test formulation. The reference control is composed of the niclosamide compound in HBSS in the absence of any permeability enhancer compounds.

As used herein, the term "fold increase" designates the multiplicative effect on niclosamide compound permeability provided by the permeability enhancer. Thus, the degree of permeability enhancement may be expressed either as a percentage of the permeability of niclosamide compound alone (in the absence of a permeability enhancing compound or in the presence of a compound which is ineffective in enhancing its permeability), in which case a result of 100% or less indicates no enhancement in permeability. Likewise, these values can be reported as a "fold" value in which 1-fold is equivalent to niclosamide compound alone (i.e., the same as 100%), a 1.5-fold value is the same as 150% of the value for niclosamide compound alone, a fold value of 5 is the equivalent of 500% enhancement, and so forth.

Example 2—Proposed Initial Human Pharmacokinetic Trial (Prophetic)

To be effective, a proposed enteric-coated niclosamide compound oral dosage form should contain an adequate amount of a permeability enhancer to impact either the paracellular or transcellular transport pathways, or both. Once such a condition has been identified, the amount of niclosamide compound can be appropriately scaled to achieve the desired blood level. For example, the amount of permeability enhancer should take into account the volume of a human duodenum: 750-1000 mg and 1500-2000 mg of enhancer should roughly correspond to the dose at the lower and upper ranges, respectively, of the proportionate volume of the human duodenum.

An initial human PK trial can be designed to evaluate the permeability enhancing function of compounds such as glycerol (e.g., glycerol monocaprylate), dimethylpalmityl-ammonio propanesulfonate (PPS), and cyclodextrin. A four- or five-way crossover protocol utilizing enteric-coated softgels is contemplated. This involves dosing subjects with either one or two softgels in separate arms and examining the PK data to determine if the niclosamide compound blood levels are dose-proportional. Niclosamide compound dose proportionality would indicate a near saturating effect from the lower dose of the permeability enhancer used. Alternatively, separate dosage forms can be manufactured for each arm wherein the niclosamide compound is kept constant and two amounts of permeability enhancer is used.

It is anticipated that results from this trial will provide useful information to demonstrate the potential to deliver the niclosamide compound orally and to use as a guide in defining an optimized formulation and niclosamide compound drug load.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A solid oral dosage form consisting of niclosamide or a pharmaceutically acceptable salt thereof, dimethylpalmityl-ammonio propanesulfonate as a permeability enhancer, and a pharmaceutically acceptable carrier, and an enteric- or pH-sensitive coating or layer,
   wherein the enteric- or pH-sensitive coating or layer surrounds the dosage form, and
   wherein the permeability enhancer increases bioavailability of niclosamide or a pharmaceutically acceptable salt thereof by at least 1.5 times the amount of the bioavailability of niclosamide or a pharmaceutically acceptable salt thereof in the absence of the permeability enhancer.

2. The solid oral dosage form of claim 1, wherein the pharmaceutically acceptable carrier is selected from the group consisting of: water, saline, oil, ethanol, dimethyl sulfoxide, gelatin, magnesium stearate, dextrose, cellulose, sugars, calcium carbonate, glycerol, alumina, and starch.

3. The solid oral dosage form of claim 1, wherein the enteric coating comprises one or more enteric polymers selected from the group consisting of: cellulose acetate phthalate, cellulose acetate trimellitate, hydroxypropyl methylcellulose acetate succinate, hydroxypropyl methylcellulose phthalate, polyvinyl acetate phthalate; and anionic polymer comprising methacrylic acid and methacrylic acid esters.

4. The solid oral dosage form of claim 1, wherein the solid oral dosage form is a tablet.

* * * * *